US00PP17913P2

(12) United States Plant Patent
Berlin

(10) Patent No.: US PP17,913 P2
(45) Date of Patent: Aug. 14, 2007

(54) ***DRACAENA* PLANT NAMED 'SOL'**

(50) Latin Name: *Dracaena fragrans*
Varietal Denomination: Sol

(76) Inventor: Erick Berlin, SJO 2795, Box 025216, Miami, FL (US) 33102

( * ) Notice: Subject to any disclaimer, the term of this patent is extended or adjusted under 35 U.S.C. 154(b) by 514 days.

(21) Appl. No.: 10/861,642

(22) Filed: Jun. 5, 2004

(51) Int. Cl.
*A01H 5/00* (2006.01)

(52) U.S. Cl. ..... Plt./383

(58) Field of Classification Search ..... Plt./383
See application file for complete search history.

(56) References Cited

PUBLICATIONS

GTITM UPOVROM Citation for 'SOL' as per QZ PBR 010544; Mar. 19, 2001.*

* cited by examiner

*Primary Examiner*—Kent Bell
(74) *Attorney, Agent, or Firm*—Mark P. Bourgeois

(57) ABSTRACT

A new cultivar of *Dracaena* plant named 'Sol' that is characterized by variegated leaves with a yellow center and green margins and a lorate shape.

1 Drawing Sheet

Botanical classification: *Dracaena fragrans*.
Variety denomination: 'Sol'.

BACKGROUND OF THE INVENTION

The present invention relates to a new and distinct cultivar of *Dracaena* plant botanically known as *Dracaena fragrans* and hereinafter referred to by the cultivar name 'Sol'.

The new cultivar was covered in 1994 by the inventor in a cultivated area of Porton de Iberia, Costa Rica. 'Sol' was discovered as a naturally occurring branch mutation of *Dracaena frangrans* 'Stedneri' (not patented).

Asexual reproduction by cuttings of the new cultivar 'Sol' were taken in 1996 in Porton de Iberia, Costa Rica.

Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Dracaena* cultivar 'Sol'. These traits in combination distinguish 'Sol' as a new and distinct cultivar.

1. *Dracaena* 'Sol' exhibits variegated leaves with yellow center stripes and green margins.
2. *Dracaena* 'Sol' exhibits an upright habit.
3. *Dracaena* 'Sol' exhibits leaves with a lorate shape.

The new cultivar 'Sol' is distinguishable from the parent *Dracaena*, by the following characteristics:

1. 'Sol' has a yellow center with green margins, the leaves of the parent plant are all green.
2. 'Sol' grows slower.
3. 'Sol' has a brown cane with yellow-white stripes on the stem, the cane of the parent plant is all brown.

BRIEF DESCRIPTION OF THE DRAWING

The accompanying photograph illustrates the distinguishing traits of *Dracaena* 'Sol'. The plant in the photograph shows an overall view of a 7 month old plant. The photograph was taken using conventional techniques and although colors may appear different from actual colors due to light reflectance, it is as accurate as possible by conventional photographic techniques.

BOTANICAL DESCRIPTION OF THE PLANT

The following is a detailed description of the new *Dracaena* cultivar named 'Sol'. Data was collected in Boskoop, The Netherlands from plants grown in Porton de Iberia, Costa Rica. The plants were 4 month old outdoor grown plants in 17 cm diameter containers. The temperature ranged from 12 to 32° Centigrade. The light level was natural outdoor light and there were no photographic treatments or growth retardants used. Color determinations are in accordance with The Royal Horticultural Society Colour Chart 2001 edition, except where general color terms of ordinary dictionary significance are used. The growing requirements are similar to the species. 'Sol' has not been tested under all possible conditions and phenotypic differences may be observed with variations in environmental, climatic, and cultural conditions, however, without any variance in genotype.

Botanical classification: *Dracaena fragrans* 'Sol'.
Parentage: 'Sol' is a naturally occurring branch mutation of *Dracaena frangrans* 'Stedneri'.
Annual or perennial: Perennial.
Use: Ornamental.
Vigor: Moderate.
Growth habit: Upright.
Plant shape: Inverted triangle.
Suitable container size: 17 cm container.
Height: Average 45 cm. in height.
Width: Average 45 cm. in width.
Hardiness: USDA Zone 10.
Growth rate: Approximately 10 cm. per month.
Propagation: Cuttings.
Time to initiate roots: Approximately 21 days to produce roots on an initial cutting.

Time to produce a rooted cutting or liner: Approximately 35 days.

Crop time: Approximately 12 weeks to produce a finished plant from a rooted cutting.

Root system: Fine and fibrous.

Root color: Orange brown 175A to 175B.

Stem:

*Stem length.*—Average 15 cm.

*Stem diameter.*—Average 1 cm.

*Stem strength.*—Very strong.

*Stem color.*—138C with stripes N138B.

*Stem pubescence.*—Absent.

*Internode length.*—Average 5.0 mm.

*Stem shape.*—Round.

*Stem surface.*—Dull, smooth, leaf scars visible on stems.

Foliage:

*Texture.*—Smooth, glossy, slightly leatherly.

*Leaf arragement.*—Alternate.

*Compound or single.*—Single.

*Quantity of leaves.*—Average 19.

*Leaf shape.*—Lorate.

*Leaf apex.*—Apiculate.

*Leaf base.*—Broad cuneate.

*Leaf length.*—Average 28 cm. in length.

*Leaf width.*—Average 6.3 cm. in width.

*Pubescence.*—Absent.

*Leaf margin.*—Entire.

*Vein pattern.*—Parallel.

*Young leaf color* (*lower surface*).—Yellow 4C with a 2 cm. wide center band 138B, margins 143A that are 3 mm. wide.

*Young leaf color* (*upper surface*).—Yellow 5C to 6C with a 2 cm. wide center band 143A with stripes N138B, margins 143A that are 3 mm. wide.

*Mature leaf color* (*lower surface*).—Yellow 10B with a 1.7 cm. wide center band 137D to 138A, margins 143A that are 3 mm. wide.

*Mature leaf color* (*upper surface*).—Yellow 10A to 11A with a 1.7 cm. wide center band 146A to 146B stripes 146D, margins 146A that are 3 mm. wide.

*Vein color.*—144A.

*Leaf attachment.*—Sessile.

*Durability of foliage to stress.*—High.

Flower: Flowering has not been observed.

Disease and pest resistance: 'Sol' has not been observed for disease or pest resistance.

It is claimed:

1. A new and distinct variety of *Dracaena* plant named 'Sol' as described and illustrated.

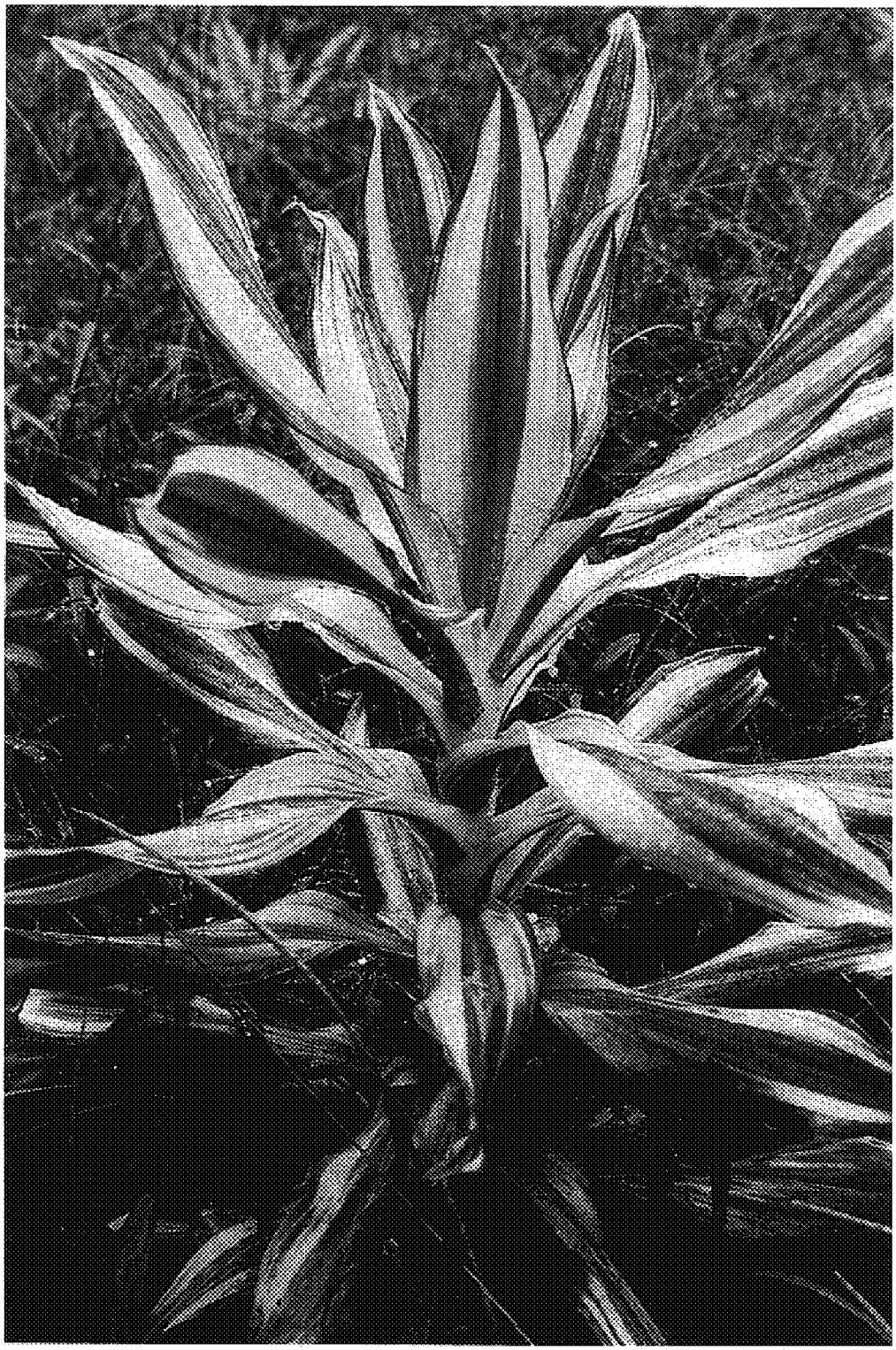

* * * * *